United States Patent
Guyonnet et al.

(10) Patent No.: US 11,331,289 B2
(45) Date of Patent: May 17, 2022

(54) ANTIMICROBIAL COMPOSITION

(71) Applicants: CEVA SANTE ANIMALE, Libourne (FR); UNION THERAPEUTICS A/S, Hellerup (DK)

(72) Inventors: Jérôme Guyonnet, Libourne (FR); Claudine Zemiriline, Libourne (FR); Pascal Butty, Libourne (FR)

(73) Assignees: CEVA SANTE ANIMALE, Libourne (FR); UNION THERAPEUTICS A/S, Hellerup (DK)

( * ) Notice: Subject to any disclaimer, the term of this patent is extended or adjusted under 35 U.S.C. 154(b) by 252 days.

(21) Appl. No.: 16/647,200

(22) PCT Filed: Sep. 14, 2018

(86) PCT No.: PCT/EP2018/074863
§ 371 (c)(1),
(2) Date: Mar. 13, 2020

(87) PCT Pub. No.: WO2019/053180
PCT Pub. Date: Mar. 21, 2019

(65) Prior Publication Data
US 2020/0323801 A1    Oct. 15, 2020

(30) Foreign Application Priority Data

Sep. 15, 2017 (EP) .................................... 17191465
Sep. 20, 2017 (EP) .................................... 17192055

(51) Int. Cl.
*A61K 31/167* (2006.01)
*A61K 9/00* (2006.01)
*A61K 47/20* (2006.01)
*A61P 31/04* (2006.01)

(52) U.S. Cl.
CPC .......... *A61K 31/167* (2013.01); *A61K 9/0014* (2013.01); *A61K 47/20* (2013.01); *A61P 31/04* (2018.01)

(58) Field of Classification Search
CPC .... A61K 31/167; A61K 9/0014; A61K 47/20; A61P 31/04
USPC ........................................ 514/563
See application file for complete search history.

(56) References Cited

FOREIGN PATENT DOCUMENTS

| WO | 2013/182990 | 12/2013 |
|----|-------------|---------|
| WO | 2016/038035 | 3/2016 |

OTHER PUBLICATIONS

English translation of WO2013182990A1: Oxyclozanide-based veterinary composition for administration to the skin [online], [retrieved on Jan. 7, 2022] Retrieved from the Internet, URL: https://patents.google.com/patent/WO2013182990A1/en (Year: 2022).*
James O. Noxon, "Chapter 13—Topical Dermatology Therapy", Handbook of Veterinary Pharmacology, Jul. 22, 2008, pp. 295-320.
International Search Report and Written Opinion of the ISA for PCT/EP2018/074863 dated Dec. 3, 2018, 14 pages.

* cited by examiner

*Primary Examiner* — Kristin A Vajda
(74) *Attorney, Agent, or Firm* — Nixon & Vanderhye P.C.

(57) ABSTRACT

The present invention relates to a new topical composition comprising niclosamide and/or oxyclozanide and to the use of said composition for the treatment or prevention of pyoderma or dermatitis in non-human mammals.

13 Claims, No Drawings

ANTIMICROBIAL COMPOSITION

This application is the U.S. national phase of International Application No. PCT/EP2018/074863 filed Sep. 14, 2018 which designated the U.S. and claims priority to EP Application No. 17191465.8 filed Sep. 15, 2017, and EP Application No. 17192055.6 filed Sep. 20, 2017, the entire contents of each of which are hereby incorporated by reference.

FIELD OF THE INVENTION

The present invention relates to a new topical composition comprising niclosamide and/or oxyclozanide and to the use of said composition for the treatment or prevention of pyoderma or dermatitis in non-human mammals.

BACKGROUND OF THE INVENTION

Animal skin is constantly exposed and attacked by pathogenic microorganisms. As a first line of defense against such attacks, the thick animal's epidermis presents a slightly basic pH, and a relatively low water content associated with the presence of antibiotic peptides having a bactericidal action. Nevertheless, changes in the structure of the epidermis, such as increased moisture or skin wounds, generally lead to the colonization and infection of the skin by pathogenic microorganisms and will often evolve towards pyoderma.

Canine pyoderma represents a common group of skin diseases characterized by bacterial infection of the skin. In the vast majority of cases, the causative organism is *Staphylococcus pseudintermedius,* though other staphylococcal species (e.g. *S. aureus, S. schleiferi*) may also be involved. Non-staphylococcal bacteria (e.g. *Streptococcus, Corynebacterium, Micrococcus, Proteus, Escherichia coli* and *Pseudomonas aeruginosa* can also be isolated from affected skin.

*Staphylococcus pseudintermedius* is a normal resident of canine mucous membranes and is thought to colonize the skin surface transiently in healthy dogs. Most cases of canine pyoderma are associated with underlying causes, such as cutaneous damage, inflammatory skin disease and primary conditions causing immune compromise. It is a frequent complication of atopic dermatitis.

As such, even following complete resolution pyoderma has a tendency to recur if the underlying disease is not properly addressed. A number of different clinical manifestations of canine pyoderma are recognized based on lesion type and distribution. Classification by lesion depth is considered useful, because the choice of antimicrobial therapy may vary according to the cutaneous tissue layers affected.

Treatment of canine pyoderma has been traditionally based on systemic antibacterial administration for 3-4 weeks, with topical antimicrobial therapy suggested as an adjunctive treatment. The guidelines recommend amoxicillin-clavulanic acid, cephalexin or clindamycin as first-line empirical agents for systemic antibiotic therapy.

With a general decrease of antibiotic-susceptibility of bacterial pathogens and specifically of *Staphylococcus pseudintermedius* associated with canine pyoderma, the treatment of these cases is becoming more and more challenging. Since the first report of Methicillin-resistant strains in 1999 (i.e. strains resistant to all members of betalactam family), an increasing number of resistant *Staphylococcus pseudintermedius* strains has been reported around the world. The prevalence of such strains among clinical isolates varies greatly, from 8.2% to 47.9% depending on geographical locations and kind of practices (generalist practitioners or referral).

With the rise of antimicrobial resistance in small animal clinical practice, topical therapy has become an important component of rational antimicrobial use for management of superficial bacterial infections. Recent studies now support recommendations to use antiseptics as the sole treatment of uncomplicated superficial skin infections.

WO2016038035 discloses the topical use of halogenated salicylanilides in topical prevention or treatment of an infection or disease caused by Gram positive bacteria. However, WO2016038035 focuses on a very specific type of topical medication via creams, foams, gels, droplets, lotions and ointments that is spread specifically on affected areas of the skin. The problem with this approach is that when applied to dogs, these local topical treatments are subject to licking of the drug thereby reducing the efficacy of the treatment and may even cause safety concern for the animal.

Therefore, there is still a need in the industry for a powerful antibiotic treatment of canine pyoderma which is easy to apply, which is long acting so that a limited number of application may be necessary to complete the treatment, which is efficient in treating pyoderma and even pyoderma caused by multi-resistant bacteria, which can be applied topically but far away from the specific area of the skin to be treated (i.e.: in an area out of licking reach), and which does not lead to resistance development because of excellent treatment compliance.

SUMMARY OF THE INVENTION

Surprisingly, the present inventors found a topical composition comprising at least one halogenated salicylanilide and DMSO in a solvent comprising diethylene glycol monomethyl ether that is extremely efficient in allowing the distribution of oxyclozanide through the surface of the skin of an animal, thereby allowing a spot on or a line on application for the treatment of pyoderma. Therefore, there is no need for a local treatment of the area affected by pyoderma, but a single application of the composition via line on or spot on close to the infected area, or on the back of the animal between the shoulders, allows diffusion of the active into any area of the animal skin that is affected by the pyoderma with a limited systemic exposure to the drug.

In a first aspect, the object of the present invention is a topical veterinary spot on or line on composition comprising 2 to 20 wt/v % of at least one halogenated salicylanilide, or a pharmaceutically acceptable salt or hydrate thereof, 35 to 55 wt/v % dimethyl sulfoxide, wherein the at least one halogenated salicylanilide is selected from niclosamide and/or oxyclozanide and wherein the composition is dissolved in diethylene glycol monomethyl ether.

Also provided is a topical veterinary spot on or line on composition for use in the treatment or prevention of pyoderma or dermatitis in non-human mammals, wherein said composition comprises 2 to 20 wt/v % of at least one halogenated salicylanilide, or a pharmaceutically acceptable salt or hydrate thereof, 35 to 55 wt/v % dimethyl sulfoxide, wherein the at least one halogenated salicylanilide is selected from niclosamide and/or oxyclozanide, and wherein the composition is dissolved in diethylene glycol monomethyl ether.

Also provided is a method of preventing and or treating pyoderma or dermatitis comprising applying topically via a spot on or line composition comprising 2 to 20 wt/v % of at least one halogenated salicylanilide, or a pharmaceutically acceptable salt or hydrate thereof, 35 to 55 wt/v % dimethyl sulfoxide, wherein the at least one halogenated salicylanilide is selected from niclosamide and/or oxyclozanide, and wherein the composition is dissolved in diethylene glycol monomethyl ether.

DETAILED DESCRIPTION OF THE INVENTION

The following terms used in the specification and claims below have the following meaning as described herein.

The terms "treating" or "treatment" in the context of this invention refers to relief, eradication, or prevention of pathology, a condition, or a disease. It may include the prevention of the disease or infection caused by Gram-positive bacteria, the suppression or relief of one or more of the symptoms of a disease or infection caused by Gram-positive bacteria such as pyoderma or dermatitis, the reduction or eradication of a non-symptomatic Gram positive bacterial colonization from an area on the body, the reduction or eradication of Gram-positive bacteria from a symptomatic skin infection, the reduction or eradication of Gram-positive bacteria colonizing an area of the body affected by a skin condition other than a skin infection (e.g. colonization of an inflammatory skin condition such as an area of skin affected by dermatitis e.g. atopic dermatitis), the suppression or relief of one or more symptoms of disease caused by Gram-positive bacteria from an area of the body affected by another non-infectious disease (e.g. an inflammatory skin condition such as an atopic dermatitis skin lesion), prevention of Gram-positive bacterial infection of skin affected by an inflammatory skin condition (e.g. prevention of infection of a dermatitis lesion), and prevention of Gram-positive bacterial infection of skin damaged by trauma (e.g. wounds, burns, stings or bites), by surgery, by medical devices (e.g. needles, catheters or cannulas etc.) or skin affected by a condition which compromises the barrier function of the skin.

The term "pharmaceutically acceptable salt" refers to salts that retain the biological effectiveness and properties of the compounds described herein and, which are not biologically or otherwise undesirable. Pharmaceutically acceptable salts are well known to skilled persons in the art.

In a first aspect, this invention relates, to a topical veterinary spot on or line on composition comprising 2 to 20 wt/v % of at least one halogenated salicylanilide, or a pharmaceutically acceptable salt or hydrate thereof, 35 to 55 wt/v % of dimethyl sulfoxide, wherein the at least one halogenated salicylanilide is selected from niclosamide and/or oxyclozanide and wherein the composition is dissolved in diethylene glycol monomethyl ether.

In the context of the present invention, a "topical medication" is a medication that is applied to body surfaces such as the skin or mucous membranes. Topical medications differ from many other types of drugs because mishandling them can lead to certain complications for the animal or the administrator of the drug.

The composition according to the present invention is administered via spot on or line-on. Spot on means that the total amount of the composition is delivered on one single place on the skin of the animal. Line on means that the composition is applied on the skin of the animal, from the base of the tail along the spine to the shoulder blades, or from the middle of the back along the spine to the shoulder blades, or less. The length of the "line-on" application can for example be 30 cm, or 20 cm, or 15 cm, or 10 cm, or 5 cm, the preferred length being 10 cm. Spot on or line on composition are formulated as a unit dose adapted to the weight and/or size of the animal, and the entire dose is applied to the animal at once.

Halogenated salicylanilides are amides of salicylic acid and aniline. Both niclosamide and oxyclozanide are chlorinated derivatives. Preferred halogenated salicylanilides according to the present invention in view of their antimicrobial profile against canine staph species are niclosamide and oxyclozanide, even most preferred is the oxyclozanide.

The composition according to the present invention comprises 2 to 20 wt/v % of at least one halogenated salicylanilide. This means 5 to 20 grams of solute per 100 milliliter of the final solution. Preferably, the composition comprises 5 to 15 wt/v %, more preferably, 8 to 12 wt/v % of the at least one halogenated salicylanilide, and even more preferably, 9 to 11 wt/v %.

The composition according to the present invention further comprises 35 to 55 wt/v % of dimethyl sulfoxide, preferably 30 to 50 wt/v %, even more preferably about 45 wt/v % DMSO.

The term about used for any numerical value throughout this invention means +/−10% of the value; e.g.: about 10 means 9 to 11.

The spot on or line on composition as described herein comprises a diffusion solvent vehicle that enables, by a simple application to one or more points of the cutaneous surface, diffusion over the entirety thereof and at the level of the sebaceous glands. The solvent system preferentially, consisting of a complex of DMSO/Transcutol and oxyclozanide, stored in these sebaceous glands diffuses progressively with the sebum product to the surface of the skin.

The composition may contain further solvents commonly known in the art to enhance solubility of the halogenated salicynalinide, as well as additional excipients such as emulsifiers, surfactants, humectants, preservatives, buffers, antioxidants, or colorants. Preferred additional excipient according to the present invention is monoethanolamine.

All embodiments described above for the composition according to the present invention also apply to the use of said composition, and to the method of treatment.

In another embodiment, the present invention relates to a topical veterinary spot on or line on composition comprising 2 to 20 wt/v % of at least one halogenated salicylanilides, or a pharmaceutically acceptable salt or hydrate thereof, 35 to 55 wt/v % of dimethyl sulfoxide, wherein the at least one halogenated salicylanilide is selected from niclosamide and/or oxyclozanide, and wherein the composition is dissolved in diethylene glycol monomethyl ether for use in the treatment or prevention of pyoderma or dermatitis in non-human mammals, wherein the composition is topically applied to the non-human mammal as a single application optionally repeated a number of times every 5 to 10 days.

Pyoderma is a pyogenic cutaneous bacterial infection due to Staphylococcal species, including *S. pseudointermedius, S. schleiferi, S. aureus,* and *S. lugdunensis*. It is very often secondary to an underlying disease process, mainly demodicosis, allergic skin disease, and endocrinopathy. Therefore, whenever the word pyoderma is used throughout this application, it is meant to encompass all of these aspects.

Pyoderma as claimed in the present application includes surface, superficial and deep pyoderma. Pyoderma according to the present application is preferably canine pyoderma and includes pyotraumatic dermatitis, impetigo (superficial pustular dermatitis), superficial bacterial folliculitis, chin pyoderma (canine acne), skin fold dermatitis (intertrigo, skin fold pyoderma), mucocutaneous pyoderma, nasal pyoderma, bacterial pododermatitis, canine pedal furunculosis (interdigital bullae, interdigital pyogranuloma). Most preferably, the pyoderma is surface and superficial pyoderma.

The topical veterinary spot on or line on composition for use according to the present invention is topically applied to the non-human mammal as a single application optionally repeated a number of times every 5 to 10 days. Preferably, it is applied to the non-human mammal once every 5 to 10 days for 3 to 6 consecutive weeks. More preferably the composition is applied once every 6 to 8 days for 3 to 6 consecutive weeks, and even more preferably once per week for 3 to 6 consecutive weeks. The treatment may be repeated as often as necessary and longer treatment periods may be necessary for deep pyoderma. Overall treatment duration is 1 to 6 weeks, preferably 3 to 6 weeks, more preferably 4 to 5 weeks, even more preferably, about 4 weeks. Treatment duration can be easily determined by the person skilled in the art as it is applied for 1 week after all the clinical signs have disappeared.

The non-human mammal is preferably a companion animal, more preferably, it is a dog or a cat, even more preferably, it is a dog.

The topical veterinary spot on or line on composition for use according to the present invention delivers 10 to 800 mg of halogenated salicylanilide, preferably 50 to 500 mg, even more preferably, about 200 mg of halogenated salicylanilide.

The topical veterinary spot on or line on composition for use according to the present invention is applied at a dose of 0.5 to 5 ml per 10 kg of body weight, preferably, 1 to 3 ml per 10 Kg of body weight, even more preferably, about 2 ml per 10 Kg of body weight. The composition is formulated as a unit dose adapted to the weight and/or size of the non-human mammal and the entire dose is applied to the animal.

In a further embodiment, the present invention refers to a method of preventing and or treating pyoderma or dermatitis comprising applying topically via a spot on or line on a composition comprising 2 to 20 wt/v % of at least one halogenated salicylanilides, or a pharmaceutically acceptable salt or hydrate thereof, 35 to 55 wt/v % dimethyl sulfoxide, wherein the at least one halogenated salicylanilide is selected from niclosamide and/or oxyclozanide, and wherein the composition is dissolved in diethylene glycol monomethyl ether.

Preferably, for the method of preventing and or treating pyoderma or dermatitis according to the present invention, the treatment is topically applied a single time and the treatment optionally repeated a number of times every 5 to 10 days.

EXAMPLES

Example 1: Line-on or Spot on Compositions A to I According to the Present Invention Example 2: Time Killing Curves of Oxyclozanide Against Canine Isolates of *Staphylococcus aureus* and *Staphylococcus pseudointermedius*

Oxyclozanide VETRANAL was from SIGMA.

In this study, 2 *Staphylococcus aureus* and 2 *Staphylococcus pseudintermedius* were tested. These strains were chosen after determination of the Minimum Inhibitory Concentration (MIC) of Oxyclozanide using broth microdilution method. The MIC of Oxyclozanide for *Staphylococcus aureus* no 16302 and no 16315 are equal to 0.5 µg/ml. The MIC of Oxyclozanide for *Staphylococcus pseudintermedius* no 15401 and no 15410 are equal to 0.125 µg/ml.

The time-killing curve is used to determine the bactericidal or bacteriostatic activity of the antibimicrobial substances. Time-killing curves of Oxyclozanide against canine isolates of *Staphylococcus aureus* and *Staphylococcus pseudintermedius* were obtained using broth macrodilution method. After contact of different fixed amounts of Oxyclozanide with an inoculum, viable bacteria are counted immediately after contact and after 1, 3, 6 and 24 hours. Counting is performed on agar medium without antimicrobial substance.

Results are analyzed by plotting $\log_{10}$ CFU/ml versus time for each tested concentration. Bactericidal activity as defined by 99.9% killing of the inoculum is determined from time-killing curves by noting the presence of a ≥3 $\log_{10}$ decrease in CFU/ml.

Bacterial strains were sub-cultured twice from one cryobead on Mueller Hinton agar and incubated at 37° C. for 18-24 hours. From the second subcultures, isolated colonies were transferred into tubes containing 2 ml of Mueller Hinton Broth in order to obtain bacterial suspensions at $10^8$ CFU/ml, knowing that an optical density of 0.1 at 620 nm corresponds to bacterial suspension at $10^8$ CFU/ml. Then, bacterial suspensions were adjusted between 5 $10^7$ and 1 $10^8$ CFU/ml by dilution in Mueller Hinton broth.

For each concentration of Oxyclozanide to be tested, 50 µl of working solution concentrated 100× and 10 µl of inoculum were added to 5 ml of Mueller-Hinton broth. Thus, the range of tested concentrations was from 0.125 to 8 µg/ml and the concentration of micro-organism was between 1 $10^6$ and 2 $10^6$ CFU/ml.

At the same time, a tube without Oxyclozanide was prepared: 50 µl of DMSO and 100 µl of inoculum were added to 5 ml of Mueller-Hinton broth and used as growth control. Tubes were incubated at 36° C. under agitation.

The numbers of viable bacteria were determined immediately after contact (TO) and after 1, 3, 6 and 24 h of incubation.

At each time, samples of each tube were taken and dilutions were performed in Mueller-Hinton broth. Then, dilutions were spread on Mueller Hinton agar with spiral plater. After 18 h of incubation at 36° C., counting of colonies was performed with automatic colony counter which determine the concentrations of viable bacteria. The

|  | A | B | C | D | E | F | G | H | I |
|---|---|---|---|---|---|---|---|---|---|
| Oxyclozanide (wt/v %) | 8 | 9 | 10 | 12 | 15 | 20 | 2 | 5 | 11 |
| DMSO (wt/v %) | 40 | 42 | 46 | 45 | 45 | 46 | 40 | 40 | 45 |
| Monoethanolamine | 3 | — | — | — | — | 3 | 3 | — | — |
| Transcutol P (QSP) | Qsp | Qsp | Qsp | Qsp | Qsp | Qsp | Qsp | Qsp | Qsp |

Trancutol P is diethylene glycol monomethyl ether also known as 2-(2-Ethoxyethoxy)ethanol.

technique employed made it possible to quantify bacterial concentrations as low as 20 CFU/ml.

Time-killing curves were plotted for each concentration of Oxyclozanide using Microsoft Excel software. The number or surviving bacteria was expressed as $\log_{10}$ CFU/ml. The time-killing curves of each strain represent the decrease in the viable bacteria count as a function of time for the Oxyclozanide concentrations concerned.

Bactericidal activity as defined by 99.9% killing of the inoculum is determined from time-killing curves by noting the presence of a ≥3 $\log_{10}$ decrease in CFU/ml.

Numbers of viable bacteria for each strain are shown in Tables (1a to 1d).

TABLE 1a

*S. aureus* n° 16 302. Viable bacteria count (CFU/ml) and ($\log_{10}$ CFU/ml) as well as bacterial reducing rate ($\Delta \log_{10}$ CFU/ml) are shown. Bacterial reducing rate = $\log_{10}$ viable count − $\log_{10}$ initial count.

| Time (h) | 0 | 1 | 3 | 6 | 24 |
|---|---|---|---|---|---|
| Viable bacteria count (CFU/ml) | | | | | |
| Control *S. aureus* n° 16 302 | $1.5\,10^6$ | $2.5\,10^6$ | $1.6\,10^7$ | $1.3\,10^9$ | $2.0\,10^9$ |
| Oxyclozanide 0.25 µg/ml (½ MIC) | $2.8\,10^6$ | $2.8\,10^6$ | $2.9\,10^6$ | $1.0\,10^7$ | $1.4\,10^8$ |
| Oxyclozanide 0.5 µg/ml (MIC) | $2.9\,10^6$ | $3.0\,10^6$ | $2.9\,10^6$ | $1.5\,10^6$ | $1.4\,10^8$ |
| Oxyclozanide 1 µg/m (2 MIC) | $2.6\,10^6$ | $2.7\,10^6$ | $2.7\,10^6$ | $1.5\,10^6$ | $7.3\,10^7$ |
| Oxyclozanide 2 µg/ml (4 MIC) | $2.9\,10^6$ | $3.0\,10^6$ | $2.5\,10^6$ | $9.1\,10^5$ | $1.1\,10^4$ |
| Oxyclozanide 4 µg/ml (8 MIC) | $3.5\,10^6$ | $2.0\,10^6$ | $6.4\,10^5$ | $1.5\,10^4$ | $2.4\,10^2$ |
| Oxyclozanide 8 µg/ml (16 MIC) | $3.2\,10^6$ | $4.6\,10^5$ | $1.5\,10^4$ | $4.6\,10^2$ | <20 |
| Viable bacteria count ($\log_{10}$ CFU/ml) | | | | | |
| Control *S. aureus* n° 16 302 | 6.2 | 6.4 | 7.2 | 9.1 | 9.3 |
| Oxyclozanide 0.25 µg/ml (½ MIC) | 6.4 | 6.4 | 6.5 | 7.0 | 8.1 |
| Oxyclozanide 0.5 µg/ml (MIC) | 6.5 | 6.5 | 6.5 | 6.2 | 8.1 |
| Oxyclozanide 1 µg/m (2 MIC) | 6.4 | 6.4 | 6.4 | 6.2 | 7.9 |
| Oxyclozanide 2 µg/ml (4 MIC) | 6.5 | 6.5 | 6.4 | 6.0 | 4.0 |
| Oxyclozanide 4 µg/ml (8 MIC) | 6.5 | 6.3 | 5.8 | 4.2 | 2.4 |
| Oxyclozanide 8 µg/ml (16 MIC) | 6.5 | 5.7 | 4.2 | 2.7 | 1.3 |
| Bacteria reducing rate | | | | | |
| Oxyclozanide 0.25 µg/ml (½ MIC) | | 0.0 | 0.1 | 0.6 | 1.7 |
| Oxyclozanide 0.5 µg/ml (MIC) | | 0.0 | 0.0 | −0.3 | 1.6 |
| Oxyclozanide 1 µg/m (2 MIC) | | 0.0 | 0.0 | −0.2 | 1.5 |
| Oxyclozanide 2 µg/ml (4 MIC) | | 0.0 | −0.1 | −0.5 | −2.5 |
| Oxyclozanide 4 µg/ml (8 MIC) | | −0.2 | −0.7 | −2.3 | −4.1 |
| Oxyclozanide 8 µg/ml (16 MIC) | | −0.8 | −2.3 | −3.8 | −5.2 |

TABLE 1b

*S. aureus* n° 16 315 Viable bacteria count (CFU/ml) and ($\log_{10}$ CFU/ml) as well as bacterial reducing rate ($\Delta \log_{10}$ CFU/ml) are shown. Bacterial reducing rate = $\log_{10}$ viable count − $\log_{10}$ initial count.

| Time (h) | 0 | 1 | 3 | 6 | 24 |
|---|---|---|---|---|---|
| Viable bacteria count (CFU/ml) | | | | | |
| Control *S. aureus* n° 16 315 | $3.1\,10^6$ | $3.0\,10^6$ | $1.2\,10^8$ | $1.3\,10^9$ | $4.3\,10^9$ |
| Oxyclozanide 0.25 µg/ml (½ MIC) | $2.7\,10^6$ | $5.1\,10^6$ | $4.6\,10^6$ | $1.2\,10^7$ | $1.7\,10^8$ |
| Oxyclozanide 0.5 µg/ml (MIC) | $2.9\,10^6$ | $2.6\,10^6$ | $4.0\,10^6$ | $2.1\,10^6$ | $9.2\,10^6$ |
| Oxyclozanide 1 µg/m (2 MIC) | $3.0\,10^6$ | $3.0\,10^6$ | $4.0\,10^6$ | $1.5\,10^6$ | $1.8\,10^5$ |
| Oxyclozanide 2 µg/ml (4 MIC) | $2.8\,10^6$ | $3.4\,10^6$ | $3.6\,10^6$ | $1.8\,10^5$ | $1.2\,10^4$ |
| Oxyclozanide 4 µg/ml (8 MIC) | $2.8\,10^6$ | $2.6\,10^6$ | $5.3\,10^5$ | $4.3\,10^4$ | 20 |
| Oxyclozanide 8 µg/ml (16 MIC) | $2.2\,10^6$ | $2.3\,10^6$ | $6.4\,10^4$ | $1.1\,10^4$ | <20 |
| Viable bacteria count ($\log_{10}$ CFU/ml) | | | | | |
| Control *S. aureus* n° 16 315 | 6.5 | 6.5 | 8.1 | 9.1 | 9.6 |
| Oxyclozanide 0.25 µg/ml (½ MIC) | 6.4 | 6.7 | 6.7 | 7.1 | 8.2 |
| Oxyclozanide 0.5 µg/ml (MIC) | 6.5 | 6.4 | 6.6 | 6.3 | 7.0 |
| Oxyclozanide 1 µg/m (2 MIC) | 6.5 | 6.5 | 6.6 | 6.2 | 5.3 |
| Oxyclozanide 2 µg/ml (4 MIC) | 6.4 | 6.5 | 6.6 | 5.3 | 4.1 |
| Oxyclozanide 4 µg/ml (8 MIC) | 6.4 | 6.4 | 5.7 | 4.6 | 1.3 |
| Oxyclozanide 8 µg/ml (16 MIC) | 6.3 | 6.4 | 4.8 | 4.0 | 1.3 |
| Bacteria reducing rate | | | | | |
| Oxyclozanide 0.25 µg/ml (½ MIC) | | 0.3 | 0.3 | 0.7 | 1.8 |
| Oxyclozanide 0.5 µg/ml (MIC) | | −0.1 | 0.1 | −0.2 | 0.5 |
| Oxyclozanide 1 µg/m (2 MIC) | | 0.0 | 0.1 | −0.3 | −1.2 |

TABLE 1b-continued

*S. aureus* n° 16 315 Viable bacteria count (CFU/ml) and ($\log_{10}$ CFU/ml) as well as bacterial reducing rate ($\Delta \log_{10}$ CFU/ml) are shown. Bacterial reducing rate = $\log_{10}$ viable count − $\log_{10}$ initial count.

| Time (h) | 0 | 1 | 3 | 6 | 24 |
|---|---|---|---|---|---|
| Oxyclozanide 2 µg/ml (4 MIC) | | 0.1 | 0.2 | −1.1 | −2.3 |
| Oxyclozanide 4 µg/ml (8 MIC) | | 0.0 | −0.7 | −1.8 | −5.1 |
| Oxyclozanide 8 µg/ml (16 MIC) | | 0.1 | −1.5 | −2.3 | −5.0 |

TABLE 1c

*S. pseudointermedius* n °15 401 Viable bacteria count (CFU/ml) and ($\log_{10}$ CFU/ml) as well as bacterial reducing rate ($\Delta \log_{10}$ CFU/ml) are shown. Bacterial reducing rate = $\log_{10}$ viable count − $\log_{10}$ initial count.

| Time (h) | 0 | 1 | 3 | 6 | 24 |
|---|---|---|---|---|---|
| Viable bacteria count (CFU/ml) | | | | | |
| Control *S. pseudointermedius* n °15 401 | $1.2\ 10^6$ | $1.5\ 10^6$ | $9.6\ 10^6$ | $3.6\ 10^8$ | $2.2\ 10^9$ |
| Oxyclozanide 0.125 µg/ml (MIC) | $8.8\ 10^5$ | $1.5\ 10^6$ | $1.2\ 10^7$ | $1.3\ 10^8$ | $4.7\ 10^8$ |
| Oxyclozanide 0.25 µg/ml (2 MIC) | $9.4\ 10^5$ | $1.4\ 10^6$ | $5.8\ 10^6$ | $1.6\ 10^8$ | $1.9\ 10^7$ |
| Oxyclozanide 0.5 µg/ml (4 MIC) | $9.4\ 10^5$ | $1.3\ 10^6$ | $2.7\ 10^6$ | $3.7\ 10^7$ | $2.8\ 10^7$ |
| Oxyclozanide 1 µg/m (8 MIC) | $9.2\ 10^5$ | $1.3\ 10^6$ | $9.2\ 10^5$ | $1.5\ 10^6$ | $4.7\ 10^6$ |
| Oxyclozanide 2 µg/ml (16 MIC) | $9.2\ 10^5$ | $8.2\ 10^5$ | $8.4\ 10^5$ | $2.1\ 10^6$ | $7.7\ 10^5$ |
| Oxyclozanide 4 µg/ml (32 MIC) | $8.4\ 10^5$ | $9.0\ 10^5$ | $7.3\ 10^5$ | $1.6\ 10^5$ | $3.2\ 10^2$ |
| Oxyclozanide 8 µg/ml (64 MIC) | $9.2\ 10^5$ | $3.8\ 10^5$ | $2.0\ 10^3$ | $4.0\ 10^1$ | <20 |
| Viable bacteria count ($\text{Log}_{10}$ CFU/ml) | | | | | |
| Control *S. pseudointermedius* n °15 401 | 6.1 | 6.2 | 7.0 | 8.6 | 9.3 |
| Oxyclozanide 0.125 µg/ml (MIC) | 5.9 | 6.2 | 7.1 | 8.1 | 8.7 |
| Oxyclozanide 0.25 µg/ml (2 MIC) | 6.0 | 6.1 | 6.8 | 8.2 | 7.3 |
| Oxyclozanide 0.5 µg/ml (4 MIC) | 6.0 | 6.1 | 6.4 | 7.6 | 7.4 |
| Oxyclozanide 1 µg/m (8 MIC) | 6.0 | 6.1 | 6.0 | 6.2 | 6.7 |
| Oxyclozanide 2 µg/ml (16 MIC) | 6.0 | 5.9 | 5.9 | 6.3 | 5.9 |
| Oxyclozanide 4 µg/ml (32 MIC) | 5.9 | 6.0 | 5.9 | 5.2 | 2.5 |
| Oxyclozanide 8 µg/ml (64 MIC) | 6.0 | 5.6 | 3.3 | 1.6 | 1.3 |
| Bacteria reducing rate | | | | | |
| Oxyclozanide 0.125 µg/ml (MIC) | | 0.3 | 1.2 | 2.2 | 2.8 |
| Oxyclozanide 0.25 µg/ml (2 MIC) | | 0.1 | 0.8 | 2.2 | 1.3 |
| Oxyclozanide 0.5 µg/ml (4 MIC) | | 0.1 | 0.4 | 1.6 | 1.4 |
| Oxyclozanide 1 µg/m (8 MIC) | | 0.1 | 0.0 | 0.2 | 0.7 |
| Oxyclozanide 2 µg/ml (16 MIC) | | −0.1 | −0.1 | 0.3 | −0.1 |
| Oxyclozanide 4 µg/ml (32 MIC) | | 0.1 | 0.0 | −0.7 | −3.4 |
| Oxyclozanide 8 µg/ml (64 MIC) | | −0.4 | −2.7 | −4.4 | −4.7 |

TABLE 1d

*S. pseudointermedius* n °15 410 Viable bacteria count (CFU/ml) and ($\log_{10}$ CFU/ml) as well as bacterial reducing rate ($\Delta \log_{10}$ CFU/ml) are shown. Bacterial reducing rate = $\log_{10}$ viable count − $\log_{10}$ initial count.

| Time (h) | 0 | 1 | 3 | 6 | 24 |
|---|---|---|---|---|---|
| Viable bacteria count (CFU/ml) | | | | | |
| Control *S. pseudointermedius* n °15 410 | $1.9\ 10^6$ | $3.2\ 10^6$ | $2.8\ 10^7$ | $1.5\ 10^9$ | $2.7\ 10^9$ |
| Oxyclozanide 0.125 µg/ml (MIC) | $1.8\ 10^6$ | $2.9\ 10^6$ | $2.3\ 10^7$ | $4.2\ 10^8$ | $1.7\ 10^9$ |
| Oxyclozanide 0.25 µg/ml (2 MIC) | $1.5\ 10^6$ | $2.2\ 10^6$ | $1.9\ 10^7$ | $2.9\ 10^8$ | $1.9\ 10^7$ |
| Oxyclozanide 0.5 µg/ml (4 MIC) | $1.4\ 10^6$ | $1.6\ 10^6$ | $1.6\ 10^7$ | $1.5\ 10^8$ | $1.5\ 10^7$ |
| Oxyclozanide 1 µg/m (8 MIC) | $1.9\ 10^6$ | $2.5\ 10^6$ | $2.4\ 10^6$ | $2.6\ 10^6$ | $5.3\ 10^6$ |
| Oxyclozanide 2 µg/ml (16 MIC) | $2.0\ 10^6$ | $2.2\ 10^6$ | $1.5\ 10^6$ | $2.5\ 10^5$ | $3.8\ 10^4$ |
| Oxyclozanide 4 µg/ml (32 MIC) | $2.1\ 10^6$ | $1.4\ 10^6$ | $1.5\ 10^6$ | $1.2\ 10^5$ | $2.6\ 10^2$ |
| Oxyclozanide 8 µg/ml (64 MIC) | $2.2\ 10^6$ | $1.4\ 10^6$ | $4.6\ 10^4$ | $3.6\ 10^2$ | <20 |
| Viable bacteria count ($\text{Log}_{10}$ CFU/ml) | | | | | |
| Control *S. pseudointermedius* n °15 410 | 6.3 | 6.5 | 7.4 | 9.2 | 9.4 |
| Oxyclozanide 0.125 µg/ml (MIC) | 6.3 | 6.5 | 7.4 | 8.6 | 9.2 |
| Oxyclozanide 0.25 µg/ml (2 MIC) | 6.2 | 6.3 | 7.3 | 8.5 | 7.3 |

TABLE 1d-continued

S. pseudointermedius n °15 410 Viable bacteria count (CFU/ml) and
($\log_{10}$ CFU/ml) as well as bacterial reducing rate ($\Delta \log_{10}$ CFU/ml) are shown.
Bacterial reducing rate = $\log_{10}$ viable count − $\log_{10}$ initial count.

| Time (h) | 0 | 1 | 3 | 6 | 24 |
|---|---|---|---|---|---|
| Oxyclozanide 0.5 µg/ml (4 MIC) | 6.1 | 6.2 | 7.2 | 8.2 | 7.2 |
| Oxyclozanide 1 µg/m (8 MIC) | 6.3 | 6.4 | 6.4 | 6.4 | 6.7 |
| Oxyclozanide 2 µglml (16 MIC) | 6.3 | 6.3 | 6.2 | 5.4 | 4.6 |
| Oxyclozanide 4 µg/ml (32 MIC) | 6.3 | 6.1 | 6.2 | 5.1 | 2.4 |
| Oxyclozanide 8 µglml (64 MIC) | 6.3 | 6.1 | 4.7 | 2.6 | 1.3 |
| Bacteria reducing rate | | | | | |
| Oxyclozanide 0.125 µg/ml (MIC) | | 0.2 | 1.1 | 2.3 | 2.9 |
| Oxyclozanide 0.25 µg/ml (2 MIC) | | 0.1 | 1.1 | 2.3 | 1.1 |
| Oxyclozanide 0.5 µg/ml (4 MIC) | | 0.1 | 1.1 | 2.1 | 1.1 |
| Oxyclozanide 1 µg/m (8 MIC) | | 0.1 | 0.1 | 0.1 | 0.4 |
| Oxyclozanide 2 µglml (16 MIC) | | 0.0 | −0.1 | −0.9 | −1.7 |
| Oxyclozanide 4 µg/ml (32 MIC) | | −0.2 | −0.1 | −1.2 | −3.9 |
| Oxyclozanide 8 µglml (64 MIC) | | −0.2 | −1.6 | −3.7 | −5.0 |

In conclusion, Pharmacodynamic profile of Oxyclozanide against *Staphylococcus aureus* and *Staphylococcus pseudintermedius* can be classified as concentration-dependant. As defined in CLSI guideline, bactericidal activity is determined by noting the presence of a ≥3 $\log_{10}$ decrease in CFU/ml. Thus, for both strains, bactericidal effect is observed after 24 hours of contact for concentration of 4 µg/ml and from 6 to 24 hours of contact for concentration of 8 µg/ml.

Example 3: Time Killing Curves of Oxyclozanide Against Four Strains of Methicillin Resistant *S. aureus* (MRSA) and Methicillin-Resistant *Staph pseudointermedius*

The objective of this study is to assess in vitro the time-killing curves of oxyclozanide against four strains of Methicillin-Resistant *Staphylococcus* from dogs.

Two Methicillin-Resistant *Staphylococcus aureus* (MRSA) and two Methicillin-Resistant *Staphylococcus pseudintermedius* (MRSP) isolated from the clinics have been tested.

The assessment of time-killing curves has been realized by a broth macrodilution method (Mueller-Hinton II Broth).

Oxyclozanide is diluted in (DMSO) into sterile tubes in order to obtain the following concentrations from 800 to 6.25 µg/ml. Those concentrations and stock standard solution are then diluted (1/10) in Mueller-Hinton II Broth in order to obtain the following concentrations from 160 to 0.06 µg/ml (See Table 2).

TABLE 2

Oxyclozanide concentration in solution and in broth madia.

| Volume of source (ml) | Volume of diluent (ml) | Concentration of solution (µg/ml) | In broth media (µg/ml), 1/10 dilution: |
|---|---|---|---|
| 1600 | 1 | 1 | 1600 | 160 |
| 1600 | 1 | 1 | 800 | 80 |
| 1600 | 1 | 3 | 400 | 40 |
| 1600 | 1 | 7 | 200 | 20 |
| 200 | 1 | 1 | 100 | 10 |
| 200 | 1 | 3 | 50 | 5 |
| 200 | 1 | 7 | 25 | 2.5 |
| 25 | 1 | 1 | 12.5 | 1.25 |
| 25 | 1 | 3 | 6.25 | 0.625 |

Each operation is performed under sterile conditions. Each working standard solution (10*the final active ingredient concentration) is distributed in tubes (1 ml, for a final volume of 10 ml after addition of 9 ml of inoculum). One tube without active ingredient is used as growth control (Concentration=0).

Bacterial isolates are sub-cultured from one cryobead on Columbia agar supplemented with 5% of blood. Pure cultures are incubated during 18-24 hours at 37° C. Three to five isolated colonies of similar appearance are selected from a previous culture and transferred into tubes containing 9 ml of Mueller-Hinton II Broth. The broth is incubated during 12-18 hours at 37° C. 0.5 to 1 ml of this broth is inoculated to another Mueller-Hinton II Broth 9 ml tube which is incubated during 3 to 4 hours at 37° C. to reach the exponential growth phase. The bacterial inoculum grown exponential phase is suspended to an optical density of McFarland standard scale 0.5 equivalent to a bacterial density of $10^8$ CFU/ml and then adjusted to a concentration of about $5.10^5$ CFU/ml as indicated by the guideline CLSI M26-A and to a second inoculum tested: $10^6$ CFU/ml.

Inoculation of Broth Tubes 9 ml of bacterial inoculum grown to exponential phase is added to 1 ml of active ingredient (or Mueller Hinton II Broth for the growth control). Tubes are incubated at 35° C. during 24 hours.

At times 0, 2, 4, 6 and 24 hours, 100 µl of broth of each tube is sampled and diluted in microplates:

Each well is re-cultured by streaking 10 µl on Columbia agar supplemented with 5% of blood. Plates are incubated at 37° C. during 18-24 hours incubation. Thus, residual bacterial concentrations are determined (CFU/ml). Results are expressed in $\log_{10}$ values of CFU/ml over-time in broth. Due to the procedure used, the minimal bacterial concentration that can be assessed is $10^2$ CFU/ml.

Individual counting results obtained for each strain are noted in the following tables 3 to 6.

TABLE 3

Counting results of MRSA strains at 5.10⁵ CFU/ml (i) 16116; (ii) 16110

| Oxyclo MIC (µg/ml) | Oxyclo- concentrations | Time (hours) | | | | |
|---|---|---|---|---|---|---|
| | | 0 | 2 | 4 | 6 | 24 |
| (i) | | | | | | |
| 0.5 | Control 0 | 3.900E+05 | 2.700E+06 | 3.400E+07 | 3.700E+08 | 5.500E+10 |
| | 1 MIC | 3.900E+05 | 1.700E+06 | 2.500E+07 | 1.600E+08 | 1.300E+08 |
| | 2 MIC | 3.900E+05 | 1.200E+05 | 1.300E+04 | 1.400E+04 | 3.500E+06 |
| | 4 MIC | 3.900E+05 | 6.000E+03 | 6.000E+02 | 4.000E+02 | 1.000E+02 |
| | 8 MIC | 3.900E+05 | 5.000E+02 | 1.000E+02 | 1.000E+02 | 1.000E+02 |
| | 16 MIC | 3.900E+05 | 3.000E+02 | 1.000E+02 | 3.000E+02 | 1.000E+02 |
| | ½ MIC | 3.900E+05 | 1.700E+06 | 3.000E+07 | 1.400E+08 | 2.600E+08 |
| | ¼ MIC | 3.900E+05 | 2.000E+06 | 4.000E+07 | 3.000E+08 | 1.900E+09 |
| (ii) | | | | | | |
| 1 | Control 0 | 4.100E+05 | 5.500E+06 | 6.800E+07 | 3.000E+10 | 4.300E+10 |
| | 1 MIC | 4.100E+05 | 9.300E+04 | 6.500E+04 | 1.100E+05 | 6.100E+05 |
| | 2 MIC | 4.100E+05 | 3.300E+03 | 1.800E+03 | 4.000E+02 | 1.000E+02 |
| | 4 MIC | 4.100E+05 | 3.000E+02 | 1.000E+02 | 1.000E+02 | 1.000E+02 |
| | 8 MIC | 4.100E+05 | 2.000E+02 | 1.000E+02 | 1.000E+02 | 1.000E+02 |
| | 16 MIC | 4.100E+05 | 1.000E+02 | 1.000E+02 | 1.000E+02 | 1.000E+02 |
| | ½ MIC | 4.100E+05 | 6.300E+05 | 9.900E+06 | 3.100E+07 | 1.900E+08 |
| | ¼ MIC | 4.100E+05 | 1.400E+06 | 9.500E+07 | 1.600E+08 | 1.100E+09 |

TABLE 4

Counting results of MRSA strains at 10⁶ CFU/ml (i) 16116; (ii) 16110

| Oxyclo MIC (µg/ml) | Oxyclo- concentrations | Time (hours) | | | | |
|---|---|---|---|---|---|---|
| | | 0 | 2 | 4 | 6 | 24 |
| (i) | | | | | | |
| 0.5 | Control 0 | 1.500E+06 | 1.000E+07 | 1.600E+08 | 1.900E+09 | 7.200E+10 |
| | 1 MIC | 1.500E+06 | 3.300E+05 | 3.900E+05 | 1.600E+06 | 2.700E+07 |
| | 2 MIC | 1.500E+06 | 2.200E+04 | 1.400E+03 | 5.000E+02 | 5.900E+05 |
| | 4 MIC | 1.500E+06 | 2.000E+02 | 2.000E+02 | 1.000E+02 | 1.000E+02 |
| | 8 MIC | 1.500E+06 | 1.000E+02 | 1.000E+02 | 1.000E+02 | 1.000E+02 |
| | 16 MIC | 1.500E+06 | 3.000E+02 | 1.000E+02 | 1.000E+02 | 1.000E+02 |
| | ½ MIC | 1.500E+06 | 3.000E+06 | 3.600E+07 | 2.300E+08 | 3.100E+08 |
| | ¼ MIC | 1.500E+06 | 2.800E+06 | 2.600E+07 | 3.000E+08 | 3.900E+08 |
| (ii) | | | | | | |
| 1 | Control 0 | 2.000E+06 | 4.400E+06 | 1.200E+08 | 2.600E+09 | 9.300E+10 |
| | 1 MIC | 2.000E+06 | 8.300E+04 | 3.400E+04 | 3.500E+03 | 7.900E+06 |
| | 2 MIC | 2.000E+06 | 4.000E+02 | 2.000E+02 | 1.000E+02 | 1.000E+02 |
| | 4 MIC | 2.000E+06 | 1.000E+02 | 1.000E+02 | 1.000E+02 | 1.000E+02 |
| | 8 MIC | 2.000E+06 | 1.000E+02 | 1.000E+02 | 1.000E+02 | 1.000E+02 |
| | 16 MIC | 2.000E+06 | 2.000E+02 | 1.000E+02 | 1.000E+02 | 1.000E+02 |
| | ½ MIC | 2.000E+06 | 6.900E+05 | 4.300E+06 | 4.800E+07 | 3.700E+07 |
| | ¼ MIC | 2.000E+06 | 8.000E+06 | 4.000E+07 | 2.400E+07 | 4.100E+07 |

TABLE 5

Counting results of MRSP strains at 5.10⁵ CFU/ml (i) 16125; (ii) 16127

| Oxyclo MIC (µg/ml) | Oxyclo- concentrations | Time (hours) | | | | |
|---|---|---|---|---|---|---|
| | | 0 | 2 | 4 | 6 | 24 |
| (i) | | | | | | |
| 0.5 | Control 0 | 4.000E+05 | 8.000E+05 | 5.500E+06 | 5.300E+07 | 5.200E+10 |
| | 1 MIC | 4.000E+05 | 2.600E+04 | 1.900E+04 | 1.300E+04 | 6.000E+05 |
| | 2 MIC | 4.000E+05 | 1.000E+02 | 3.000E+02 | 1.000E+02 | 2.000E+02 |
| | 4 MIC | 4.000E+05 | 1.000E+02 | 1.000E+02 | 1.000E+02 | 1.000E+02 |
| | 8 MIC | 4.000E+05 | 1.000E+02 | 1.000E+02 | 1.000E+02 | 1.000E+02 |

TABLE 5-continued

Counting results of MRSP strains at $5.10^5$ CFU/ml (i) 16125; (ii) 16127

| Oxyclo MIC (µg/ml) | Oxyclo- concentrations | \multicolumn{5}{c}{Time (hours)} | | | | |
|---|---|---|---|---|---|---|
| | | 0 | 2 | 4 | 6 | 24 |
| | 16 MIC | 4.000E+05 | 1.000E+02 | 1.000E+02 | 1.000E+02 | 1.000E+02 |
| | ½ MIC | 4.000E+05 | 3.800E+05 | 3.100E+05 | 3.400E+05 | 3.200E+08 |
| | ¼ MIC | 4.000E+05 | 5.500E+05 | 2.600E+06 | 1.600E+07 | 4.900E+10 |
| (ii) | | | | | | |
| 0.25 | Control 0 | 3.600E+05 | 3.800E+05 | 2.200E+06 | 1.300E+08 | 5.200E+10 |
| | 1 MIC | 3.600E+05 | 2.300E+05 | 1.900E+06 | 4.600E+06 | 8.100E+08 |
| | 2 MIC | 3.600E+05 | 2.000E+05 | 2.400E+05 | 2.400E+05 | 6.600E+05 |
| | 4 MIC | 3.600E+05 | 1.400E+04 | 4.400E+03 | 3.500E+03 | 1.300E+03 |
| | 8 MIC | 3.600E+05 | 1.600E+03 | 4.000E+02 | 1.000E+02 | 1.000E+02 |
| | 16 MIC | 3.600E+05 | 3.000E+02 | 1.000E+02 | 1.000E+02 | 1.000E+02 |
| | ½ MIC | 3.600E+05 | 3.300E+05 | 2.700E+06 | 2.400E+07 | 2.900E+10 |
| | ¼ MIC | 3.600E+05 | 3.900E+05 | 5.900E+06 | 3.400E+07 | 2.900E+10 |

TABLE 6

Counting results of MRSP strains at $10^6$ CFU/ml (i) 16125; (ii) 16127

| Oxyclo MIC (µg/ml) | Oxyclo- concentrations | Time (hours) | | | | |
|---|---|---|---|---|---|---|
| | | 0 | 2 | 4 | 6 | 24 |
| (i) | | | | | | |
| 0.5 | Control 0 | 1.000E+06 | 8.000E+06 | 8.000E+07 | 5.000E+08 | 5.600E+10 |
| | 1 MIC | 1.000E+06 | 1.000E+06 | 1.500E+05 | 1.000E+05 | 4.100E+06 |
| | 2 MIC | 1.000E+06 | 1.600E+03 | 1.000E+02 | 1.000E+02 | 1.000E+02 |
| | 4 MIC | 1.000E+06 | 5.000E+02 | 1.000E+02 | 1.000E+02 | 1.000E+02 |
| | 8 MIC | 1.000E+06 | 1.000E+02 | 1.000E+02 | 1.000E+02 | 1.000E+02 |
| | 16 MIC | 1.000E+06 | 1.000E+02 | 1.000E+02 | 1.000E+02 | 1.000E+02 |
| | ½ MIC | 1.000E+06 | 1.800E+06 | 2.800E+06 | 3.400E+06 | 1.900E+08 |
| | ¼ MIC | 1.000E+06 | 1.500E+06 | 1.000E+07 | 1.000E+08 | 2.600E+09 |
| (ii) | | | | | | |
| 0.25 | Control 0 | 9.000E+05 | 5.000E+06 | 1.700E+07 | 9.000E+07 | 1.000E+11 |
| | 1 MIC | 9.000E+05 | 4.100E+05 | 4.000E+06 | 7.500E+06 | 9.000E+07 |
| | 2 MIC | 9.000E+05 | 4.100E+05 | 5.400E+05 | 2.500E+06 | 7.600E+06 |
| | 4 MIC | 9.000E+05 | 1.700E+04 | 1.500E+03 | 3.000E+02 | 8.000E+02 |
| | 8 MIC | 9.000E+05 | 5.200E+03 | 1.000E+02 | 1.000E+02 | 1.000E+02 |
| | 16 MIC | 9.000E+05 | 1.200E+03 | 1.000E+02 | 1.000E+02 | 1.000E+02 |
| | ½ MIC | 9.000E+05 | 4.300E+05 | 3.700E+06 | 2.100E+07 | 3.400E+09 |
| | ¼ MIC | 9.000E+05 | 5.100E+05 | 4.200E+06 | 3.000E+07 | 4.900E+10 |

To conclude, time-kill profiles are nearly similar for the two inocula tested for a strain considered and between the four strains tested : concentration-dependent bactericidal effect for concentrations >=2 MIC. Bactericidal effect as defined by the CLSI M26-A Guideline ("A bactericidal effect can be seen by a>=3 $\log_{10}$ (99.9% killing) decrease in CFU at the time specified") is observed as following for concentrations of 4 MIC.

| | Strain/Inoculum | Time to obtain bactericidal effect at 4 MIC |
|---|---|---|
| MRSA | 16116/$5.10^5$ CFU/ml | 4 to 6 hours |
| | 16116/$10^6$ CFU/ml | 2 hours |
| | 16110/$5.10^5$ CFU/ml | 2 hours |
| | 16110/$10^6$ CFU/ml | 2 hours |
| MRSP | 16125/$5.10^5$ CFU/ml | 2 hours |
| | 16125/$10^6$ CFU/ml | 2 hours |
| | 16127/$5.10^5$ CFU/ml | 6 to 24 hours |
| | 16127/$10^6$ CFU/ml | 4 to 6 hours |

Example 4: Effect Against *Malassezia*

Isolates

Six clinical isolates from dog skin (n=5) and cats (n=1) which had been sent to EnvA (mycology laboratory of BioPôle Alfort) for mycological culture. The isolates, collected in March 2016, were identified as belonging to the species *Malassezia pachydermatis*. They were maintained by regular transplanting on medium of Sabouraud. Isolates are subcultured 2 to 3 days prior to testing sensitivity.

Experimental Protocol (Microdilution Broth Method)

A stock solution of Oxyclozanide at 1600 µg/mL is prepared in DMSO. The stock solution is then diluted in DMSO to obtain a concentration range of 3.125 µg/ml to 800 µg/ml. A 1/50 dilution of this range and of the stock solution is then carried out in ultrapure water so as to obtain a concentration range of 0.0625 µg/ml to 32 µg/ml and containing 2% of DMSO. 50 µl of these solutions are deposited in wells of a microplate and then 50 µl of inoculum calibrated at 106 CFU/ml in Sabouraud/Tween 40 (2%) are added. A range of tested concentrations ranges from 0.0312

µg/mL to 16 µg/mL. The final concentration of DMSO in contact with the inoculum is 1%. The same dilution and seeding protocol was followed with a stock solution of amphotericin B at 1600 µg/ml. A "placebo" (or yeast growth control) column is systematically included in the plates. The plates are incubated at 37 ° C. The reading is done at 24 and 48 h. Several trials were conducted and protocol adjustments were required. In particular, the concentration of the inoculum had to be reduced for antifungal activity to be observed.

TABLE 7

Counting results of *Malassezia* strains at $10^6$ CFU/ml

| | MIC of Amphoterine B (µg/mL) | | MIC of Oxyclozanide (µg/mL) | |
|---|---|---|---|---|
| | Assay 1 | Assay 2 | Assay 1 | Assay 2 |
| Isolate 1 | 2 | 4 | 8 | 4 |
| Isolate 2 | 2 | 2 | 8 | 8 |
| Isolate 3 | 4 | 8 | 8 | 16 |
| Isolate 4 | 4 | 4 | >16 | >16 |
| Isolate 5 | 4 | 4 | 8 | 8 |
| Isolate 6 | 4 | 8 | 8 | 16 |

Conclusion

Oxyclozanide is active with respect to Malassezia pachydermatis. This activity is variable according to the isolates (no activity with respect to the isolate 3) and the MIC values are high. See Table 7 for comparison. It should be emphasized that the techniques and protocols (used in the various studies published to date) are very variable with MICs ranging from 0.12 to 8 µg/mL.

Example 5: Pharmacokinetic Profile of an Oxyclozanide Spot on Composition

The aim of this study was to determine the tolerability, bioavailability and pharmacokinetic profile of the oxyclozanide by treating beagle dogs via cutaneous route of administration (with the C719 composition).

The test item (C719) was a topical solution for veterinary use with the following composition comprising: Oxyclozanide 10 g/100 mL, 46 g of Dimethyl Sulfoxide and diethylene glycol monoethyl ether (Transcutol®) q.s 100 mL.

Experimental Design

The six adult males Beagles dogs (more than 12 Kg) used in the study were in good health at inclusion examination. Their haematological-biochemical parameters were within the supplier's normal range or even within an acceptable range. Animals had not received any treatment containing anthelmintics or antibiotics from 15 days before the start of the animal phase, and no treatment from 8 days before D0.

The dogs were kept in wood shavings bedding. Animals were housed individually in order to guarantee the quality of the results by avoiding the dogs licking each other after the treatment was applied. The animals were installed in the test facility two weeks before D-1. This period allowed them to acclimatise to the living conditions (largely the same as those of the supplier found on the same site). Appropriate food (pellets) was dispensed ad libitum into the feeders. Water providers were used to ensure an ad-libitum to tap water supplying. All of the animals were housed in the same way, with particular care given to their welfare, according to the practices in place. During the 8 day period of relative isolation (the animals still had visual, olfactory and auditory contact with their peers), every effort were made to limit any stress that could be caused to the animals, with increased socialisation activities.

Treatment: The 6 dogs received the treatment on D0. The C719 product was applied line-on, uniformly along the backbone starting from the neck to the base of the tail. The product was administered to each of the 6 dogs using graduated syringes with 0.1 ml precision at a dose of 20 mg oxyclozanide/Kg, meaning 0.20 ml/Kg body weight.

Clinical assessment: On D-1 of each phase, a physical examination, including a weigh-in, was carried out to control the general statement of the dogs. Clinical observation was undertaken on a daily basis by the individual responsible for looking after the dogs. In the hour following treatment administration on D0 of each phase, clinical observation was performed. Two areas were shaved on each side 7-8 cm from the backbone, covering an area of around 30 cm x 5 cm. Shaving was reproduced at the following times: D-2, D-1, D0+24 h, D0+48 h, D0+72 h, D4, D5 and D6. The cosmetic appearance of the fur coat around the treatment area was assessed at D0+1 h, D0+3 h, D0+24 h, D0+72 h, and D7. Upon each assessment, the visual appearance of each dog's fur coat was assessed according to the following scoring system:

Moist appearance (Yes/No)
Greasy appearance (Yes/No)
Clumps of fur (Yes/No)
Deposits (Mild/Moderate/Significant)
Discoloration (describe)

Dermal tolerance was assessed following treatment on: D0+1 h, D0+3 h and D0+24 h, D0+72 h, D7. Upon each assessment, dermal tolerance in the treatment area will be assessed according to the following scoring system:

Erythema:
  No erythema
  Very mild erythema (barely visible)
  Clearly-defined erythema
  Moderate erythema
  Severe erythema (beetroot red) with slight sores (deep lesions)
Oedema (Yes/No)
Excoriation (Yes/No)
Scabs (Yes/No)

Blood sampling: For each animal, a blood sample of around 4 ml was collected from the jugular vein using tubes containing lithium heparin at the following times (with tolerance of 10%) at D-1, D0+1 h, D0+5 h, D0+9 h, D0+12 h, D0+16 h, D0+24 h, D0+32 h, D0+48 h, D0+56 h, D0+72 h, D0+80 h, D4, D5, D6 and D7. Centrifugation (around 3500 revolutions/min, for 15 minutes at +4° C.) was performed a maximum of 30 minutes after sampling. The plasma was collected and then divided into two aliquots in tubes (Nunc 1.8 ml type) as follows: S1 aliquot: around 0.5 ml; S2 aliquot: the remainder of the plasma (more than 0.5 ml). Each aliquot was identified with the CEVA study code; the identification number of animal and its case number; the aliquot number (S1 or S2); the type, date and time of sampling. The aliquots were stored at −70° C. +/−5° C. until analysis.

Skin sampling discs (D-Squame Discs): Essentially performed according to Vidémont et al.: Veterinary Dermatology, vol. 23, pp. 103-123, 2011. Tape-stripping (Adhesive films) are pressed onto the surface of the skin with a fixed amount of pressure before removal. The superficial layers of the SC adhere to the film, are stripped from the Stratum corneum are then accessible for further investigation. At the same time, repeated tape-stripping may be an effective comparative model for impaired skin barrier function.

Desquamation of the skin was performed from the left or right sided shaved areas of the back (through an alternating way), by means of a special sampling method (D-Squame Discs), which was performed at the following times (with tolerance of 10%): D-1, D0+3 h, D0+8 h, D0+24 h, D0+48 h, D0+72 h, D4, D5, D6 and D7.

Twelve 22 mm diameter discs (D-Squame Discs) were applied successively on the same well defined and previously marked area along the backbone: The discs were applied as follows:

A tweezers was used to remove carefully the discs from its backing using the edge provided.

The disc was applied on the defined area.

The disc was pressed for approximately one second using the D-Squame Pressure Instrument −150 g/cm².

In all cases, the 12 discs removed from the skin were divided into 3 samples (S1, S2 and S3) as follows:
S1: the first 2 discs were placed in a scintillation vial
S2: the following 5 discs were placed in a scintillation vial
S3: the last 5 discs were placed in a scintillation vial Each vial was identified with the CEVA study code; the identification number of animal and their case number; the vial number (S1, S2 or S3); the type, date and time of sampling.

Pharmaco Kinetic Assesment

The pharmacokinetic analyses were performed using Phoenix software (version 6.3, Pharsight, USA) which is a Microsoft-Windows based software program designed to carry out non-compartmental data modelling. Data points indicated as "missing" were systematically ignored during the calculation and therefore have no effect on the results. A missing status is assigned and no flag symbol is used. If outliers were suspected, they were identified using the Outlier identification procedure of STATGRAPHICS.

Data were analysed using non compartmental approach. The purpose of this approach is to supply an estimate of the kinetic parameters of a drug on the basis of a descriptive data analysis without making any assumption on the existence and structure of a possible mathematical model suitable for describing the observations. However, in order to perform this analysis we have to make the assumption that the terminal elimination phase of the kinetic process can be approximated by an exponential equation. This is equivalent to assuming that a straight line can approximate the semi-logarithmic transformation of data belonging to the terminal removal process of the drug in the body. On the basis of this assumption, the basic kinetic parameters of a drug based on statistical moment theory such as AUC (zero moment) and the Thalf (Elimination half-life), and others classical parameters.

The descriptive statistics were calculated per day and treatment for each concentration parameter: arithmetic mean, standard deviation, standard error of the mean, coefficient of variation (CV%), maximum and minimum. The mean concentrations and the standard deviations were calculated and the mean concentration time curves were plotted. The descriptive statistics of the pharmacokinetic parameters were calculated per treatment.

Results

Clinical observations, dermal tolerance and cosmetic assessment: After the cutaneous treatment on D0, all dogs responded well to the treatment. No significant sign appeared for dermal tolerance all along the phase. The cosmetic appearance of the fur around the treatment area was assessed. The fur was essentially moist and greasy appearance for 24 hours completed with some deposits (mild or moderate) during up to 7 days.

Oxyclozanide concentrations in blood: The mean and SD plasma concentration-time profiles of oxyclozanide are presented in Table 8. Bioavailability was low (12%) after topical application. Low concentrations of oxyclozanide were observed suggesting a little exposition of the gut flora.

TABLE 8

Mean (μg/L) plasma concentration-time of oxyclozanide obtained after single topical administration of C719 in dogs.

| Time (h) | N | Mean (ug/L) | SD (ug/L) | CV % | Min (ug/L) | Max (ug/L) |
|---|---|---|---|---|---|---|
| 0.00 | 0 | | | | | |
| 1.00 | 2 | 2213 | 2372 | 107.2 | 535 | 3890 |
| 5.00 | 5 | 469 | 624 | 133.1 | 54 | 1493 |
| 9.00 | 6 | 377 | 498 | 132.0 | 90 | 1387 |
| 12.00 | 6 | 516 | 787 | 152.5 | 149 | 2117 |
| 16.00 | 6 | 635 | 892 | 140.6 | 160 | 2437 |
| 24.00 | 6 | 639 | 712 | 111.5 | 240 | 2084 |
| 32.00 | 6 | 274 | 223 | 81.2 | 82 | 701 |
| 48.00 | 5 | 135 | 66 | 48.7 | 69 | 243 |
| 56.00 | 6 | 102 | 54 | 52.9 | 51 | 203 |
| 72.00 | 6 | 86 | 47 | 54.8 | 58 | 180 |
| 80.00 | 5 | 91 | 40 | 44.0 | 53 | 157 |
| 96.00 | 6 | 81 | 43 | 52.7 | 51 | 162 |
| 120.00 | 3 | 131 | 63 | 48.0 | 72 | 197 |
| 144.00 | 5 | 72 | 19 | 25.7 | 54 | 104 |
| 168.00 | 5 | 93 | 46 | 48.8 | 53 | 143 |

Oxyclozanide concentrations in skin: The mean and SD superficial skin concentration-time profiles of oxyclozanide are presented in the Table 9. Oxyclozanide accumulates well for a long period of time in stratum corneum following topical application. Oxyclozanide seems to evenly diffuse on the skin area of the body because there are about 10 cm between the application site and the tape-stripping areas.

TABLE 9

Mean (μg/kg) tape skin concentration-time of oxyclozanide obtained after single topical administration of C719 in dogs.

| Time (h) | N | Mean (ng/g) | SD (ng/g) | CV % | Min (ng/g) | Max (ng/g) |
|---|---|---|---|---|---|---|
| 0 | 5 | 0 | 0 | nc | 0 | 0 |
| 3 | 6 | 117782 | 70086 | 59.5 | 37774 | 190721 |
| 8 | 6 | 211917 | 170128 | 80.3 | 51920 | 502078 |
| 24 | 6 | 363216 | 163261 | 44.9 | 148170 | 575800 |
| 48 | 6 | 534732 | 312654 | 58.5 | 263882 | 973433 |
| 72 | 6 | 338554 | 197539 | 58.3 | 127635 | 528450 |
| 96 | 6 | 418740 | 292276 | 69.8 | 156853 | 864250 |
| 120 | 6 | 289573 | 134742 | 46.5 | 148142 | 473850 |
| 144 | 6 | 287380 | 238035 | 82.8 | 98741 | 724050 |
| 168 | 6 | 204411 | 59785 | 29.2 | 141178 | 296565 |

Pharmacokinetics analysis: Mean and individual pharmacokinetic parameters of oxyclozanide in plasma are summarised in the Table 10 below. The relative bioavailability of oxyclozanide after topical administration of 12% was calculated between animal treated at the dose of 20 mg/kg.

TABLE 10

Mean and individual estimated NCA parameters of oxyclozanide in plasma obtained after single topical administration of C719 in dogs.

| Subject | Half-life (h) | Tmax (h) | Cmax (ug/L) | Tlast (h) | Clast (ug/L) | AUClast (h * ug/L) |
|---|---|---|---|---|---|---|
| 2284902 | 764.7 | 24.0 | 409 | 168.0 | 70 | 18002 |
| 2284919 | 57.7 | 1.0 | 3890 | 168.0 | 53 | 85625 |

TABLE 10-continued

Mean and individual estimated NCA parameters of oxyclozanide in plasma obtained after single topical administration of C719 in dogs.

| Subject | Half-life (h) | Tmax (h) | Cmax (ug/L) | Tlast (h) | Clast (ug/L) | AUClast (h * ug/L) |
|---|---|---|---|---|---|---|
| 2292943 | 126.7 | 24.0 | 240 | 168.0 | 58 | 14559 |
| 2293355 | 105.1 | 24.0 | 353 | 168.0 | 143 | 21436 |
| 2307664 | 104.1 | 16.0 | 518 | 168.0 | 143 | 23927 |
| 2307791 | 187.1 | 5.0 | 644 | 144.0 | 65 | 17821 |
| N | 6 | 6 | 6 | 6 | 6 | 6 |
| Mean | 224.2 | 15.7 | 1009 | 164.0 | 89 | 30228 |
| SD | 268.1 | 10.4 | 1418 | 9.8 | 42 | 27330 |
| Min | 57.7 | 1.0 | 240 | 144.0 | 53 | 14559 |
| Median | 115.9 | 20.0 | 464 | 168.0 | 67 | 19719 |
| Max | 764.7 | 24.0 | 3890 | 168 | 143 | 85625 |
| CV % | 119.6 | 66.2 | 140.5 | 6.0 | 47.8 | 90.4 |

The inter-variability between animals was low after topical application. Main PK parameters are presented in Table 11 below:

TABLE 11

Mean and individual estimated NCA parameters of oxyclozanide in plasma obtained after single topical administration of C719 in dogs.

| Subject | Corr_XY | Lambda_z (1/h) | HL_Lambda_z (h) | Tmax (h) | Cmax (ug/L) | Tlast (h) | Clast (ug/L) |
|---|---|---|---|---|---|---|---|
| 2284902 | −0.139 | 0.0009 | 764.7 | 24.0 | 409 | 168.0 | 70 |
| 2284919 | −0.977 | 0.0120 | 57.7 | 1.0 | 3890 | 168.0 | 53 |
| 2292943 | −0.693 | 0.0055 | 126.7 | 24.0 | 240 | 168.0 | 58 |
| 2293355 | −0.291 | 0.0066 | 105.1 | 24.0 | 353 | 168.0 | 143 |
| 2307664 | −0.439 | 0.0067 | 104.1 | 16.0 | 518 | 168.0 | 143 |
| 2307791 | −0.382 | 0.0037 | 187.1 | 5.0 | 644 | 144.0 | 65 |
| N | 6 | 6 | 6 | 6 | 6 | 6 | 6 |
| Mean | −0.487 | 0.0059 | 224.2 | 15.7 | 1009 | 164.0 | 89 |
| SD | 0.302 | 0.0037 | 268.1 | 10.4 | 1418 | 9.8 | 42 |
| Min | −0.977 | 0.0009 | 57.7 | 1.0 | 240 | 144.0 | 53 |
| Median | −0.411 | 0.0060 | 115.9 | 20.0 | 464 | 168.0 | 67 |
| Max | −0.139 | 0.0120 | 764.7 | 24.0 | 3890 | 168 | 143 |
| CV % | −62.0 | 62.7 | 119.6 | 66.2 | 140.5 | 6.0 | 47.8 |

The inter-variability between animals was low after topical application. Main PK parameters are presented in Table 12 below:

TABLE 12

Mean and individual estimated NCA parameters of oxyclozanide in skin obtained after single topical administration of C719 in dogs.

| Subject | Half-life (h) | Tmax (h) | Cmax (ng/g) | Tlast (h) | Clast (ng/g) | AUClast (h * ng/g) | AUCINF_obs (h * ng/g) |
|---|---|---|---|---|---|---|---|
| 2284902 | 61.5 | 48.0 | 973433 | 168.0 | 182068 | 89611608 | 105769317 |
| 2284919 | 90.5 | 72.0 | 524692 | 168.0 | 233343 | 49932665 | 80409635 |
| 2292943 | 63.2 | 48.0 | 891650 | 168.0 | 296565 | 102474007 | 129514919 |
| 2293355 | 687.5 | 48.0 | 263882 | 168.0 | 227969 | 26115844 | 252223923 |
| 2307664 | 76.2 | 48.0 | 391883 | 168.0 | 141178 | 39910232 | 55434734 |
| 2307791 | 138.0 | 48.0 | 377056 | 168.0 | 145343 | 35569581 | 64509686 |
| N | 6 | 6 | 6 | 6 | 6 | 6 | 6 |
| Mean | 186.2 | 52.0 | 570433 | 168.0 | 204411 | 57268989 | 114643702 |
| SD | 247.2 | 9.8 | 293574 | 0.0 | 59785 | 31260421 | 72690189 |
| Min | 61.5 | 48.0 | 263882 | 168.0 | 141178 | 26115844 | 55434734 |
| Median | 83.4 | 48.0 | 458288 | 168.0 | 205019 | 44921448 | 93089476 |
| Max | 687.5 | 72.0 | 973433 | 168 | 296565 | 102474007 | 252223923 |
| CV % | 132.8 | 18.8 | 51.5 | 0.0 | 29.2 | 54.6 | 63.4 |

Conclusion

The specific properties of oxyclozanide (high potency and pharmacokinetic properties) as shown above allows reaching the 3 main keys of a good antibiotic to treat skin infections in dogs i) a low toxicity allowing a long duration of treatment (usually 3-4 weeks for superficial pyoderma and much longer for deep pyoderma), ii) a narrow spectrum targeting *Staphylococcus* spp or Gram Positive bacteria and without effect against Gram negative bacteria thereby preventing resistance development, iii) a distribution in skin tissue so that effective concentrations are reached.

In fact, Treatment of canine pyoderma has been traditionally based on systemic antibacterial administration for 3-4 weeks, with topical antimicrobial therapy suggested as an adjunctive treatment. The guidelines recommend amoxicillin-clavulanic acid, cephalexin or clindamycin as first line empirical agents for systemic antibiotic therapy. With a decrease of antibio susceptibility of microbial pthogens and specifically of *Staphylococcus pseudintermedius* strains associated with canine pyoderma, the treatment of these cases is becoming more and more challenging. Since the first report of Methicillin-resistant strains in 1999 (i.e. strains resistant to all members of betalactam family), an increasing number of resistant *Staphylococcus pseudintermedius* strains has been reported around the world. The prevalence of such strains among clinical isolates varies greatly, from 8.2% to 47.9% depending on geographical locations and kind of practices (generalist practitioners or referral).

As a consequence, topical therapy has become an important component of rational antimicrobial use for management of superficial bacterial infections. In the conditions of the study it can be concluded that the topical product according to the present invention shows high concentrations (at least 1000 fold the MIC) and high persistence in the stratum corneum for a long time (between 1 to 3 weeks) in all animals. These preliminary investigations have showed that a weekly dose to monthly dose as spot on can be efficient for treatment of skin infections due to *Staphylococcus* spp.

The invention claimed is:

1. A topical veterinary spot on or line on composition comprising 2 to 20 wt/v % of at least one halogenated salicylanilide, or a pharmaceutically acceptable salt or hydrate thereof, 35 to 55 wt/v % dimethyl sulfoxide, wherein the at least one halogenated salicylanilide is selected from the group consisting of niclosamide, oxyclozanide and a mixture thereof, and wherein the composition is dissolved in diethylene glycol monomethyl ether.

2. The composition according to claim 1, wherein the halogenated salicylanilide is oxyclozanide.

3. The composition according to claim 1, wherein it comprises 5 to 15 wt/v % oxyclozanide.

4. The composition according to claim 1, wherein it comprises 8 to 12 wt/v % oxyclozanide.

5. The composition according to claim 1, wherein it comprises 40 to 50 wt/v % of dimethyl sulfoxide.

6. A method for the treatment or prevention of pyoderma or dermatitis in a non-human mammal in need thereof, comprising topically applying to the non-human mammal a topical veterinary spot on or line on composition, which comprises 2 to 20 wt/v % of at least one halogenated salicylanilide, or a pharmaceutically acceptable salt or hydrate thereof, and 35 to 55 wt/v % dimethyl sulfoxide, wherein the at least one halogenated salicylanilide is selected from the group consisting of niclosamide, oxyclozanide and a mixture thereof, wherein the composition is dissolved in diethylene glycol monomethyl ether, and wherein said composition is topically applied to the non-human mammal as a single application optionally repeated a number of times every 5 to 10 days.

7. The method according to claim 6, wherein the spot on or line on composition is applied to the non-human mammal once every 5 to 10 days for 3 to 5 consecutive weeks.

8. The method according to claim 6, wherein the spot on or line on composition delivers 10 to 800 mg of halogenated salicylanilide.

9. The method according to claim 6, wherein the spot on or line on composition delivers about 200 mg of halogenated salicylanilide.

10. The method according to claim 6, wherein the spot on or line on composition is applied at a dose of 0.5 to 5 ml per 10 kg of body weight.

11. The method according to claim 6, wherein the spot on or line on composition comprises oxyclozanide.

12. The method according to claim 6, wherein the spot on or line on composition comprises 5 to 15 wt/v % oxyclozanide.

13. The method according to claim 6, wherein the spot on or line on composition comprises 40 to 50 wt/v % of dimethyl sulfoxide.

\* \* \* \* \*